US008104953B2

(12) United States Patent
Van Suetendael et al.

(10) Patent No.: US 8,104,953 B2
(45) Date of Patent: Jan. 31, 2012

(54) SYSTEMS AND METHODS FOR DETERMINING HEAT TRANSFER CHARACTERISTICS

(75) Inventors: Arthur J. Van Suetendael, Stuart, FL (US); Jeffrey Prausa, Port St. Lucie, FL (US); Jason Ostanek, State College, PA (US); Karen A. Thole, State College, PA (US)

(73) Assignee: United Technologies Corp., Hartford, CT (US)

( * ) Notice: Subject to any disclaimer, the term of this patent is extended or adjusted under 35 U.S.C. 154(b) by 572 days.

(21) Appl. No.: 12/323,644

(22) Filed: Nov. 26, 2008

(65) Prior Publication Data

US 2010/0128752 A1    May 27, 2010

(51) Int. Cl.
 *G01N 25/18* (2006.01)
(52) U.S. Cl. ............................................ 374/44; 374/43
(58) Field of Classification Search .................... 374/43, 374/44, 46, 29, 30, 5, 160, 161, 137
See application file for complete search history.

(56) References Cited

U.S. PATENT DOCUMENTS

| | | | |
|---|---|---|---|
| 4,515,896 A | 5/1985 | Melton | |
| 4,613,237 A | 9/1986 | Melton | |
| 4,730,160 A | 3/1988 | Cusack et al. | |
| 4,779,994 A | 10/1988 | Diller et al. | |
| 4,885,633 A | 12/1989 | Buck | |
| 6,648,506 B2 * | 11/2003 | McGrath et al. | 374/161 |
| 6,718,291 B1 * | 4/2004 | Shapiro et al. | 703/2 |
| 6,804,622 B2 | 10/2004 | Bunker et al. | |
| 7,040,805 B1 | 5/2006 | Ou et al. | |
| 7,069,169 B2 | 6/2006 | Nakakita et al. | |
| 7,407,325 B2 * | 8/2008 | Watanabe et al. | 374/43 |
| 2002/0020945 A1 * | 2/2002 | Cho et al. | 264/460 |
| 2004/0128016 A1 * | 7/2004 | Stewart | 700/159 |
| 2005/0114104 A1 * | 5/2005 | Friedl et al. | 703/2 |
| 2007/0043497 A1 | 2/2007 | Leogrande et al. | |
| 2009/0179355 A1 * | 7/2009 | Wicker et al. | 264/401 |
| 2010/0128752 A1 * | 5/2010 | Van Suetendael et al. | 374/44 |

* cited by examiner

*Primary Examiner* — Yaritza Guadalupe-McCall

(57) ABSTRACT

Systems and methods for determining heat transfer characteristics are provided. In this regard, a representative system for determining heat transfer characteristics includes: a stereolithographic model of a component, the model having a surface; and a test article mounted to the surface such that an extension of the test article protrudes from and is thermally insulated from the surface of the model.

20 Claims, 2 Drawing Sheets ized components. Typically, active cooling# SYSTEMS AND METHODS FOR DETERMINING HEAT TRANSFER CHARACTERISTICS

BACKGROUND

1. Technical Field

The disclosure generally relates to heat transfer analysis.

2. Description of the Related Art

Gas turbine engine components are oftentimes cooled to increase component durability. Typically, active cooling schemes are used that divert air from an associated compressor. Unfortunately, use of bleed air from a compressor has an adverse impact on the engine cycle, thereby increasing the importance of cooling efficiency.

To increase cooling efficiency, cooling features with extended surfaces are frequently added to components to increase heat transfer surface area and augment the intensity of convection. Examples include (but are not limited to) trip strips inside turbine blade cooling channels, pin fins used on combustor and exhaust liners, and pedestals used in turbine airfoil trailing edges. The accurate prediction of convective heat transfer for these cooling features at engine conditions, however, is difficult.

SUMMARY

Systems and methods for determining heat transfer characteristics are provided. In this regard, an exemplary embodiment of a method for determining heat transfer characteristics comprises: forming a polymer mold using rapid prototyping; forming a three-dimensional model of a component using the polymer mold, the model having a surface and an extension protruding therefrom, the extension being formed of a material with a melting point lower than a melting point of the polymer mold; determining a heat transfer characteristic of the surface of the model; and determining a heat transfer characteristic of the extension.

Another exemplary embodiment of a method for determining heat transfer characteristics comprises: forming a stereolithographic model of a component, the model having a surface and an extension protruding therefrom, the extension being thermally insulated from the surface; determining a heat transfer characteristic of the surface of the model; independently determining a heat transfer characteristic of the extension; and predicting heat transfer characteristics of the component based, at least in part, on the heat transfer characteristic of surface and the heat transfer characteristic of the extension.

An exemplary embodiment of a system for determining heat transfer characteristics comprises: a stereolithographic model of a component, the model having a surface; and a test article mounted to the surface such that an extension of the test article protrudes from and is thermally insulated from the surface of the model.

Other systems, methods, features and/or advantages of this disclosure will be or may become apparent to one with skill in the art upon examination of the following drawings and detailed description. It is intended that all such additional systems, methods, features and/or advantages be included within this description and be within the scope of the present disclosure.

BRIEF DESCRIPTION OF THE DRAWINGS

Many aspects of the disclosure can be better understood with reference to the following drawings. The components in the drawings are not necessarily to scale. Moreover, in the drawings, like reference numerals designate corresponding parts throughout the several views.

DETAILED DESCRIPTION

Systems and methods for determining heat transfer characteristics are provided, several exemplary embodiments of which will be described in detail. In this regard, determining heat transfer characteristics of components exhibiting complex geometries can be accomplished by determining the characteristics of a primary surface of such a component, and independently determining characteristics of any features that protrude from the primary surface. In some embodiments, Stereolithography (SLA) materials are used to form a model of a component, with one or more protuberances being modeled using material with a low Biot number. Notably, the Biot number correlates the relative magnitudes of the surface convection and internal conduction resistance to heat transfer. Thus, in contrast to forming an entire model from a material with a low Biot number, only discrete portions of the model need be formed of such a material, thereby potentially simplifying model preparation.

Figure 1:
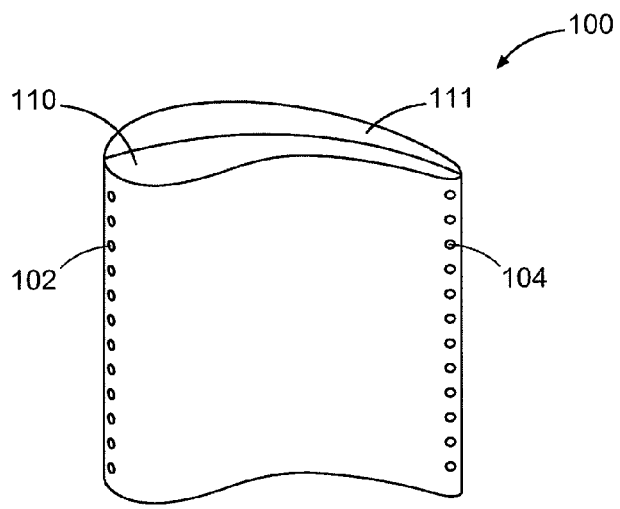
FIG. 1 is a schematic diagram depicting an exemplary embodiment of a component model.

With reference to the drawings, FIG. 1 is a schematic diagram of an exemplary embodiment of a component model. As shown in FIG. 1, model 100 is a scale model of an airfoil, which forms a portion of an actively-cooled vane of a gas turbine engine. Models, such as model 100 are not limited to vane configurations, as various other components can be modeled. However, for the purposes of discussion, the following will be limited to actively-cooled gas turbine engine components.

The vane from which model 100 is modeled incorporates internal cooling provisions that permit cooling air to flow into, through and out of the vane during operation. Notably, holes (e.g., holes 102, 104) of model 100 are representative of cooling holes of the vane. In various embodiments, various scales of models can be used. In general, model scale factor is determined to achieve accurate geometric similitude and acceptable measurement uncertainty with consideration for model manufacturability and test facility limitations. By way of example, a scale of model to component of between approximately 2× and approximately 20× is considered typical.

In the embodiment of FIG. 1, model 100 is constructed via a rapid prototyping process called Stereolithography (SLA). Although various SLA materials can be used, model 100 is formed of a transparent polymer material in order to facilitate transient liquid crystal testing.

Figure 2:
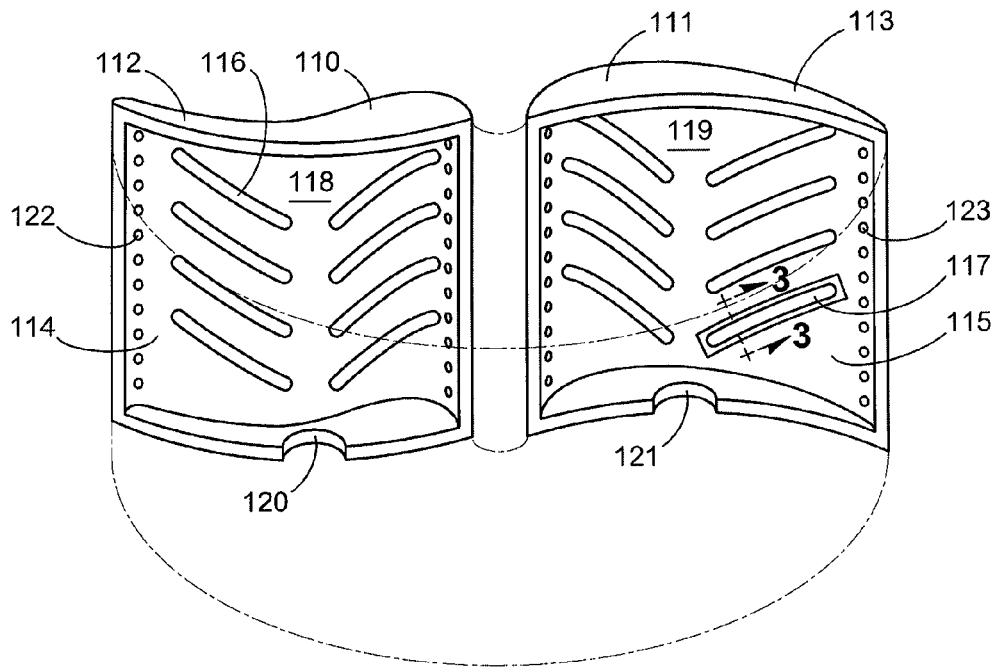
FIG. 2 is a schematic diagram depicting the model of FIG. 1, with the model opened to show detail of actively-cooled surfaces.

FIG. 2 is a schematic diagram depicting model 100, with the model opened to show detail of surfaces corresponding to actively-cooled surfaces of the vane. As shown in FIG. 2, model portions 110 and 111 are configured to engage each other to form an interior cavity. Model portions 110, 111 include exterior surfaces 112 and 113, respectively, as well as interior surfaces 114 and 115, respectively. Extensions (e.g., extensions 116, 117) protrude from primary surfaces (i.e., surfaces 118, 119) of the interior surfaces. In this embodiment, the extensions (which correspond to trip strips) are arranged in a chevron orientation along the primary surfaces. Such trip strips are configured to enhance heat transfer of the vane during operation by enhancing the mixing of the cooling air flow passing through the vane and increasing the convective surface area of the interior surfaces.

Access to the interior cavity of model 100 is provided in this embodiment by an entry orifice formed by split apertures 120, 121. Additionally, each of the model portions includes exit holes (e.g., exit holes 122, 123) that correspond to cooling holes of the modeled vane.

Figure 3:
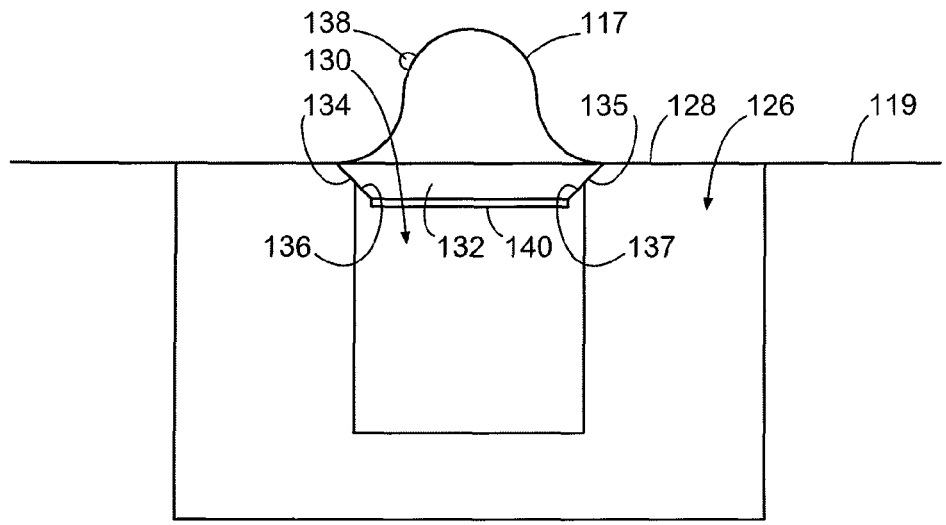
FIG. 3 is a schematic diagram depicting a cross-section of a portion of the model of FIGS. 1 and 2, as viewed along section line 3-3.

Extension 117 is shown in greater detail in FIG. 3. As shown in FIG. 3, extension 117 protrudes from surface 119 that defines a cavity 126 in which a carrier 128 is received. In this embodiment, carrier 128 is formed of insulative material that is configured to thermally isolate extension 117 from surface 119. By way of example, the carrier can be formed of polyurethane foam.

Carrier 128 includes a channel 130 that is sized and shaped to mount a base 132 of extension 117. In this embodiment, channel 130 incorporates chamfered edges 134, 135 that engage corresponding chamfered edges 136, 137 of base 132. As such, engagement of the corresponding edges of the extension and channel causes base 132 to be positioned within channel 130. Notably, the void located within the channel and beneath the extension further enhances thermal decoupling of the extension from surface 119.

Various materials can be used for forming an extension such as copper, aluminum or any material with thermal conductivity high enough to prevent significant temperature gradients from developing within the extension during testing. In the embodiment of FIG. 3, the extensions are cast using a low melting point alloy (i.e., an alloy with a melting point lower than approximately 300° F.). Use of a low melting point alloy enables the use of rapid prototyped (typically stereolithography) polymer molds for forming the castings, allowing creation of extensions with complex shapes at relatively low cost. Since heat transfer model tests are typically conducted at relatively low temperatures (i.e. between ambient and approximately 250° F.) a low melting point alloy is an acceptable material for these test articles. Additionally, various other extended features, such as fins, turbulators, pins and pedestals can be created using low melting point alloys and rapid prototyped polymer molds.

A temperature sensing device 138 (typically a thermocouple) also is provided. Specifically, device 138 is located to obtain temperature indications corresponding to the extension. In some embodiments, a single temperature sensing device can be used for each such extension, whereas in other embodiments, multiple devices or an infra-red camera can be used on a given extension.

In the embodiment of FIG. 3, extension 117 includes a heater 140 that is thermally coupled to base 132. Although various types of heaters can be used, heater 140 is a foil heater. The heater is used to heat the extension during testing, such as when using a steady state heat balance technique. For other types of testing, such as when using a transient lumped mass heat transfer technique, a heater need not be provided.

Figure 4:
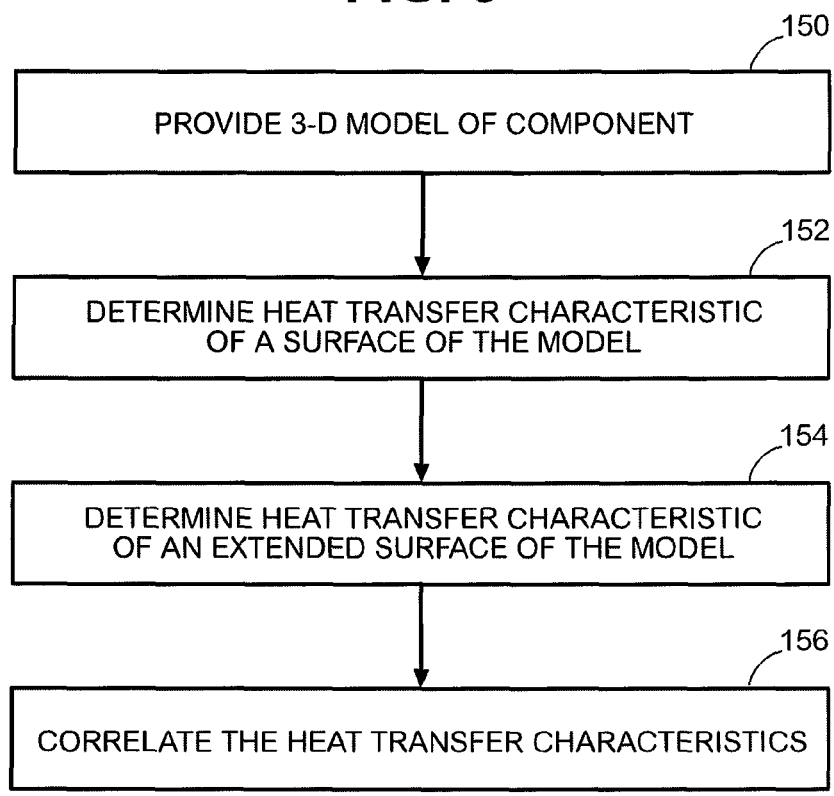
FIG. 4 is a flowchart depicting an exemplary embodiment of a method for determining heat transfer characteristics.

FIG. 4 is a flowchart depicting an exemplary embodiment of a method for determining heat transfer characteristics. As shown in FIG. 4, the method may be construed as beginning at block 150, in which a three-dimensional model of a component is provided. Specifically, the model includes a surface with an extension protruding from the surface. By way of example, the component can be an actively-cooled gas turbine engine component and the extension can correspond to a cooling enhancement feature of the component (e.g., a trip strip, fin, pin or pedestal).

In block 152, a heat transfer characteristic of the primary test surface of the model is determined. In some embodiments, this involves using a transient liquid crystal technique, in which a thermochromatic liquid crystal material is applied to the test surface of the model. Heated (or cooled) air (or other gas) is then delivered to the model, which is initially at a known temperature. The distribution of convective heat transfer on the test surface is determined from observation of the liquid crystal color play (i.e. surface temperature response) and the transient air temperature response within the model. In other embodiments, this can involve using a steady-state test approach, in which a constant heat flux is applied to the primary test surface via a heater. The temperature of the test surface is determined via thermocouples, thermochromatic liquid crystals, or infrared thermography. With knowledge of the fluid temperature within the model, convective heat transfer on the test surface is then determined via a steady-state heat balance.

In block 154, a heat transfer characteristic of the extension is determined. In some embodiments, this can involve using a steady-state approach, in which a constant heat flux is applied to the base of the extension via a heater. The temperature of the extension is determined via a temperature sensor (typically a thermocouple) and convective heat transfer on the wetted surface of the extension is determined (with knowledge of the local fluid temperature) via a steady-state heat balance. In other embodiments, this can involve using a transient lumped mass approach, in which a temperature sensor (typically a thermocouple) is installed in the extension. Heated (or cooled) air (or other gas) is then delivered to the model, which is initially at a known temperature. The air temperature response within the model is measured via temperature sensors. If the extension has a sufficiently low Biot modulus, the convective heat transfer on the wetted surface of the extension can be determined (with knowledge of the extension's geometry, mass and specific heat) via a transient heat balance. In both of the aforementioned embodiments, the extension is made of a material with high thermal conductivity and is thermally isolated from the rest of the test article, in order to reduce uncertainties resulting from temperature gradients and conduction heat losses, respectively.

Thereafter, such as depicted in block 156, the heat transfer characteristic of the primary surface and the heat transfer characteristic of the extension are each correlated. For forced convection applications (most common in gas turbine engines), Nusselt number (dimensionless heat transfer coefficient) is typically correlated as a function of Reynolds and Prandtl numbers. The correlations derived can subsequently be used to facilitate thermal analysis of gas turbine engine components (at engine operating conditions) via determination of associated convective boundary conditions.

It should be emphasized that the above-described embodiments are merely possible examples of implementations set forth for a clear understanding of the principles of this disclosure. Many variations and modifications may be made to the above-described embodiments without departing substantially from the spirit and principles of the disclosure. All such modifications and variations are intended to be included herein within the scope of this disclosure and protected by the accompanying claims.

The invention claimed is:

1. A method for determining heat transfer characteristics comprising:

forming a polymer mold using rapid prototyping;

forming a three-dimensional model of a component, the model having a surface and an extension protruding therefrom, the extension being formed using the polymer mold of a material with a melting point lower than a melting point of the polymer mold;

determining a heat transfer characteristic of the surface of the model; and determining a heat transfer characteristic of the extension.

2. The method of claim 1, wherein:

forming the polymer mold comprises forming the mold using stereolithography; and the extension comprises metal.

3. The method of claim 2, wherein the extension comprises a low melting point alloy.

4. The method of claim 1, wherein determining the heat transfer characteristic of the surface is accomplished using a technique different than a technique used to determine the heat transfer characteristic of the extension.

5. The method of claim 1, wherein the component is an actively-cooled gas turbine engine component.

6. The method of claim 5, wherein the extension corresponds to a cooling enhancement feature of the component.

7. The method of claim 1, wherein determining the heat transfer characteristic of the extension comprises thermally insulating the extension from the surface.

8. The method of claim 1, wherein determining the heat transfer characteristic of the surface comprises:

applying thermochromatic liquid crystal material to the surface; and observing the liquid crystal material to determine heat transfer characteristics of the surface.

9. The method of claim 1, wherein determining the heat transfer characteristic of the extension comprises using a temperature sensing device to measure a temperature associated with the extension.

10. A method for determining heat transfer characteristics comprising:

forming a stereolithographic model of a component, the model having a surface and an extension protruding therefrom, the extension being thermally insulated from the surface;

determining a heat transfer characteristic of the surface of the model;

independently determining a heat transfer characteristic of the extension; and predicting heat transfer characteristics of the component based, at least in part, on the heat transfer characteristic of surface and the heat transfer characteristic of the extension.

11. The method of claim 10, wherein determining the heat transfer characteristic of the surface of the model comprises performing a transient liquid crystal heat transfer test.

12. The method of claim 10, wherein determining the heat transfer characteristic of the extension comprises using steady-state heat balance testing.

13. The method of claim 10, wherein determining the heat transfer characteristic of the extension comprises using transient lumped mass testing.

14. A system for determining heat transfer characteristics comprising:

a stereolithographic model of a component, the model having a surface; and a test article mounted to the surface such that an extension of the test article protrudes from and is thermally insulated from the surface of the model.

15. The system of claim 14, wherein:

the test article has a carrier operative to mount the test article to the model; and the extension is mounted to the carrier.

16. The system of claim 15, wherein:

the carrier has an opening communicating with a recess; and the extension extends across the opening.

17. The system of claim 15, wherein the extension is formed of a low melting point alloy having a melting point lower than approximately 300° F.

18. The system of claim 14, wherein the extension is formed of Indalloy.

19. The system of claim 14, wherein:

the extension has a base, at least a portion of the base being positioned in the recess; and the test article further comprises a heater mounted to the base.

20. The system of claim 14, further comprising a temperature sensing device operative to determine a temperature of the extension.

* * * * *